US00PP31626P2

(12) United States Plant Patent
Snijder

(10) Patent No.: US PP31,626 P2
(45) Date of Patent: Mar. 31, 2020

(54) ***PELARGONIUM* PLANT NAMED 'PECZ0017'**

(50) Latin Name: *Pelargonium interspecific*
Varietal Denomination: PECZ0017

(71) Applicant: SYNGENTA PARTICIPATIONS AG, Basel (CH)

(72) Inventor: Ronald Christiaan Snijder, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/350,878

(22) Filed: Jan. 28, 2019

(51) Int. Cl.
*A01H 5/02* (2018.01)
*A01H 6/42* (2018.01)

(52) U.S. Cl.
USPC ..... Plt./330

(58) Field of Classification Search
USPC ..... Plt./263.1, 324, 325, 330
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new *Pelargonium* plant named 'PECZ0017' particularly distinguished by has deep red colored inflorescences held above the dark-green foliage, very heat and drought tolerant with continuous color through the most extreme summer heat, with a medium vigorous plant habit.

1 Drawing Sheet

Latin name of the genus and species of the plant claimed: *Pelargonium interspecific.*

Varietal denomination: 'PECZ0017'.

BACKGROUND OF THE NEW PLANT

The present invention comprises a new *Pelargonium*, botanically known as *Pelargonium interspecific*, and hereinafter referred to by the variety name 'PECZ0017'.

'PECZ0017' is a product of a planned breeding program. The new cultivar 'PECZ0017' has deep red colored inflorescences held above the dark-green foliage, very heat and drought tolerant with continuous color through the most extreme summer heat, with a medium vigorous plant habit.

'PECZ0017' originates from a hybridization in a controlled breeding program made in February 2013 in a greenhouse in Enkhuizen, The Netherlands. It resulted from a self-pollination of an unpatented, proprietary plant of *P. interspecific* parentage, identified as 'PEZ-AY0389-01' with florets with five petals and a thinner peduncle when compared to 'PECZ0017'. The resultant seed was sown in December 2014.

'PECZ0017' was selected as one flowering plant within the progeny of the stated cross in April 2014 in a greenhouse in Enkhuizen, The Netherlands.

The first act of asexual reproduction of 'PECZ0017' was accomplished when vegetative cuttings were propagated from the initial selection in the May 2014 in a greenhouse in Enkhuizen, The Netherlands.

BRIEF SUMMARY OF INVENTION

Horticultural examination of plants grown from cuttings of the plant initiated in July 2014 in Enkhuizen The Netherlands, and continuing thereafter, has demonstrated that the combination of characteristics as herein disclosed for 'PECZ0017' are firmly fixed and are retained through successive generations of asexual reproduction.

'PECZ0017' has not been observed under all possible environmental conditions. The phenotype may vary significantly with variations in environment such as temperature, light intensity, and day length.

A Plant Breeder's Right for this cultivar has not yet been applied for. 'PECZ0017' has not been made publicly available prior to the effective filing date of this application, notwithstanding any disclosure that may have been made less than one year prior to the effective filing date of this application by the inventor or another who obtained 'PECZ0017' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

Figure 1:
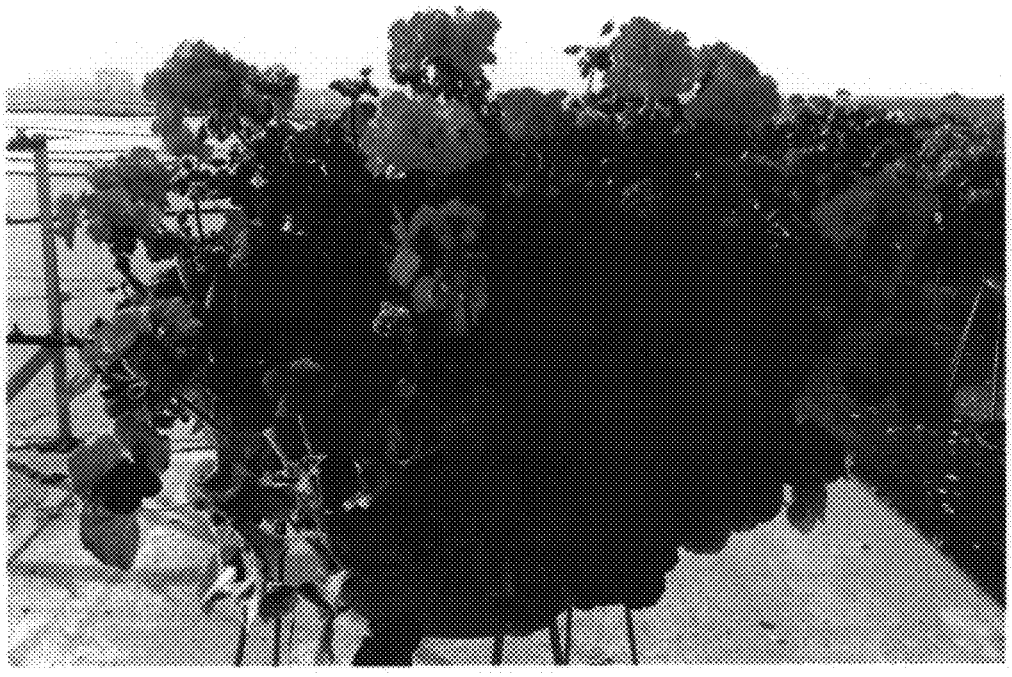
Figure 2:
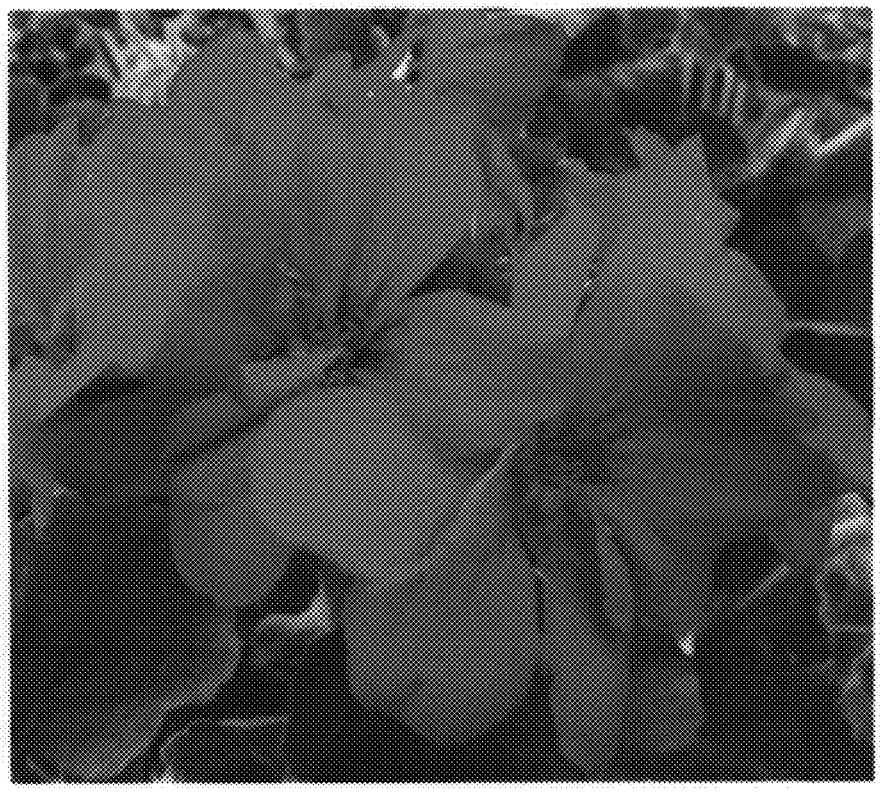

The accompanying photographic drawings show typical flower and foliage characteristics of 'PECZ0017' with colors being as true as possible with an illustration of this type. The photographic drawings in FIG. 1 shows a basket with 4 flowering plants of the new variety and in FIG. 2, a close-up of the flower.

DETAILED BOTANICAL DESCRIPTION

The plant descriptions and measurements were taken in Andijk, the Netherlands in September 2018 under natural light. These plants were approximately 12 weeks old and were grown in 1 gallon pots, in a greenhouse trial. The plants shown in the photographs were about 25 weeks old growing in a 10 inch pot in a greenhouse. The photographs were taken in October 2018.

Color references are made to The Royal Horticultural Society Colour Chart (R.H.S.) 2001.

TABLE 1

DIFFERENCES BETWEEN THE NEW VARIETY 'PECZ0017' AND A MOST SIMILAR VARIETY

| | 'PECZ0017' | 'Clip Velred' (U.S. Plant Pat. No. 20,532) |
|---|---|---|
| Leaf zone color: | RHS 202A | Very light hue of RHS 176B |
| Umbel diameter size: | 12-14 cm | 10 12 cm |

Plant:

*Form, growth and habit.*—Upright to semi-upright.
*Plant height.*—40-45 cm.
*Plant height (inflorescence included).*—45-55 cm.
*Plant width.*—35-40 cm.

Roots:

*Number of days to initiate roots.*—15-18 days at about 22 degrees C.
*Number of days to produce a rooted cutting.*—21-23 days at 22 degrees C.
*Type.*—Fine, fibrous, free branching.
*Color.*—RHS N155B but whiter.

Foliage:

*Immature leaf, color upper surface.*—Closest to RHS 136A and RHS 139A.
*Immature leaf, lower surface.*—Closest to RHS 137A and RHS 137B.
*Mature leaf, color upper surface.*—Closest to RHS 136A and RHS 139A.
*Mature leaf, color lower surface.*—Closest to RHS 137A and RHS 137B.
*Length.*—4.5-6.0 cm.
*Width.*—8.0-10.0 cm.
*Shape.*—Orbicular.
*Base shape.*—Cordate, heart-shaped.
*Apex shape.*—Rounded/waved, slightly crenate.
*Margin.*—Slightly crenate.
*Texture upper side.*—Pilose.
*Texture lower side.*—Pilose.
*Leaf zonation color.*—RHS 202A.
*Color of veins, upper surface.*—Closest to RHS 144A.
*Color of veins, lower surface.*—Closest to RHS 144A and RHS 144B.
*Pattern of veining.*—Palmate.
*Petiole color.*—Closest to RHS 144A.
*Petiole length.*—6.0-17.0 cm.
*Diameter of petiole.*—0.2-0.3 cm.
*Texture.*—Pilose, hirsute hairs.

Stem:

*Quantity of branches.*—10-13 extending from base, lateral branches not included in counting.
*Color of stem.*—Closest to RHS 144A.
*Length of stem.*—20-40 cm.
*Diameter.*—About 1.0 cm.
*Length of internodes.*—1.5-4.0 cm.
*Texture.*—Hirsute, pilose hairs.

Peduncle:

*Color of peduncle.*—Closest to RHS 144A, with anthocyanins of color closest to RHS 187B and RHS 137C.
*Length of peduncle.*—14-23 cm.
*Peduncle diameter.*—About 0.5 cm.
*Texture.*—Hirsute.

Pedicel:

*Color of pedicel.*—Closest to RHS 187B.
*Length of pedicel.*—2.5-3.0 cm.
*Diameter of pedicel.*—0.15-0.2 cm.
*Texture.*—Pilose.

Bud (just before opening):

*Color.*—Closest to RHS 45C and RHS 46C.
*Length.*—1.5-2.0 cm.
*Width.*—1.0 cm.
*Shape.*—Elliptical.

Inflorescence:

*Type.*—Umbel, semi-spherical.
*Lastingness of individual flowers.*—7-9 days at 18° C. temperature.
*Number of inflorescences per plant.*—8 mature and 11 immature umbels in various stages.
*Fragrance.*—None.
*Umbel diameter.*—12-14 cm.
*Umbel depth.*—5.0-6.0 cm.

Corolla:

*Form.*—Semi-double.
*Number of petals.*—7-9.
*Diameter of flower.*—About 5.0-5.5 cm.
*Depth of flower.*—About 1.5 cm.
*Color upper petals, upper surface.*—Between RHS 42A, RHS 45A and RHS 45B with darker marking around base (veining and spot) of color closest to RHS 187A.
*Color upper petals, lower surface.*—Closest to RHS 45C.
*Length of upper petals.*—2.8-3.2 cm.
*Width of upper petals.*—1.8-2.1 cm.
*Color lower petals, upper surface.*—Between RHS 42A, RHS 45A and RHS 45B.
*Color lower petals, lower surface.*—Closest to RHS 45C.
*Length of lower petals.*—2.4-2.7 cm.
*Width of lower petals.*—1.8-2.1 cm.
*Petal shape.*—Obovate.
*Apex shape.*—Rounded.
*Margin.*—Entire.
*Base.*—Attenuate.
*Petal texture.*—Papillose.

Calyx:

*Number of sepals.*—5.
*Color of sepals.*—Closest to RHS 144A with anthocyanins closest to RHS 187B and RHS 187C.
*Length of sepals.*—1.0-1.2 cm.
*Width of sepals.*—0.4-0.5 cm.
*Sepal shape.*—Lanceolate to enciform.
*Apex shape.*—Acute.
*Margins.*—Entire.
*Texture, upper surface.*—Pilose.
*Lower surface.*—Pilose.

Reproductive organs:

Gynoecium:

*Pistil.*—1.
*Length.*—1.0-1.1 cm.
*Style color.*—Closest to RHS 59C and RHS 60B.
*Style length.*—About 0.5-0.6 cm.
*Stigma color.*—Closest to RHS 60B.
*Ovary color.*—Closest to RHS 143A.
*Ovary length.*—About 0.4-0.5 cm.
*Ovary diameter.*—About 0.3 cm.

Androecium:

*Number of stamens.*—5.

*Color of filaments*.—Closest to RHS 60B and RHS 60C.
*Length filaments*.—1.0-1.2 cm.
*Anther color*.—Closest to RHS 60A and RHS 60B.
*Length of anthers*.—About 0.3 cm.
*Color of pollen*.—Closest to RHS 28A.
*Pollen amount*.—Normal.
*Fertility/seed set*.—Has not been determined to date.
*Disease/pest resistance*.—Has not been determined to date.

What is claimed is:

1. A new and distinct variety of *Pelargonium* plant named 'PECZ0017' substantially as illustrated and described herein.

* * * * *